United States Patent [19]

Sherba et al.

[11] Patent Number: 5,069,717
[45] Date of Patent: Dec. 3, 1991

[54] ANTIALGAL COMPOSITIONS COMPRISING DIPHENYLETHERS AND LYSOZYME, METHODS OF CONTROLLING ALGAE, AND COATING COMPOSITIONS COMPRISING THE ANTIALGAL COMPOSITIONS

[75] Inventors: Samuel E. Sherba, Willingboro, N.J.; Rai J. Mehta, Gujarat, India

[73] Assignee: Rohm and Haas Company, Philadelphia, Pa.

[21] Appl. No.: 637,084

[22] Filed: Jan. 3, 1991

[51] Int. Cl.$^5$ .............................................. C09D 5/14
[52] U.S. Cl. .............................. 106/18.35; 106/18.32; 71/67; 71/DIG. 1; 424/94.1; 424/94.61; 424/405; 435/206
[58] Field of Search ............................ 71/67, DIG. 1; 106/18.32, 18.35; 424/94.1, 94.61, 405; 435/206

[56] References Cited

U.S. PATENT DOCUMENTS

| 3,506,720 | 4/1970 | Model et al. ......................... 568/637 |
| 3,629,477 | 12/1971 | Model et al. ......................... 424/340 |
| 3,772,445 | 11/1973 | Noguchi et al. ...................... 424/340 |
| 3,787,217 | 1/1974 | Nita et al. ............................... 71/67 |
| 3,798,276 | 3/1974 | Bayer et al. ...................... 260/612 R |
| 3,908,019 | 9/1975 | Noguchi et al. ...................... 424/340 |
| 4,112,002 | 9/1978 | Schneider et al. .............. 260/612 R |
| 4,268,693 | 5/1981 | Muntwyler et al. ................. 568/637 |
| 4,339,462 | 7/1982 | Muntwyler et al. ................. 424/340 |
| 4,772,744 | 9/1988 | Bayer et al. .......................... 560/133 |

FOREIGN PATENT DOCUMENTS 48-048624 7/1973 Japan .
1592011 7/1981 United Kingdom .

OTHER PUBLICATIONS

S. D. Strause and P. R. Puckorious, Power, Sl, "Cooling-Water Treatment for Control of Scaling, Fouling, Corrosion", Jun. 1984.
Seventh Annual Congress on Marine Corrosion and Fouling, "Selecting Acting Antifouling Agents", Valenca, Spain, 11/10/88.
Boger et al., "Binding and Peroxidative Action of Oxyfluorfin in Sensitive and Tolerant Algal Species", Z. Naturforsch, 42c, 819–823 (1987).
Boger et al., "Multifunctional Mode of Action of Substituted Nitiodiphenylethers in Sceneadesmus Cells", Z. Naturforsch, 36c, 633–637 (1981).
Boger et al., "Radical Formation and Peroxidative Activity of Phytotoxic Diphenyl Ethers", Z. Naturforsch, 39c, 486–491 (1984).
Boger et al., "Variable Fluorescence and Fluorescence Spectra of Algae after Herbicide-Induced Pigment Bleaching", Z. Naturforsch, 38c, 556–562 (1983).
Boger et al., "Oxyfluorfer and Lipid Peroxidation: Protein Damage as a Phytotoxic Consequence", Weed Science, 33, 766–770 (1985).
Boger et al., "Comparison of the Bleaching Activity of Norfluorozon and Oxyfluorofen", Weed Science, 31, 338 (1983).
Boger et al., "Sites of Herbicidal Action on Photosynthesis:A Fluoresciace Assay Study: Weed Science", 29, 371–375 (1981).
Boger et al., "The Bleaching Effect of the Diphenyl Ether Oxyfluorfen", Weed Science, 29, 169–173 (1981).
Boger et al., "Herbicidal Mode of Action of Chlorophyll Formation", J. Agric Food Chem, 32, 868–872 (1984).
Boger et al., "The Diphenyl Ether Herbicide Oxyfluorfen: Action of Antioxidants", J. Agric Food Chem., 32, 725–728 (1984).
Boger et al., "Peroxidative Activity of Oxyfluorfen with Regard to Carotenoids in Scienedesmus", J. Agric Food Chem., 32, 523–525 (1984).
Boger et al., "Inhibition of Carotenogenesis by Substituted Diphenyl Ethers of the m-Phenoxybenzamide Type; Pesticide Chemistry andd Physiology", 20, 183–187 (1984).
Boger et al., "Correlation Between Structure and Phytotoxic Activities of Nitrophenyl Ethers; Pesticide Biochemistry and Physiology", 19, 309–320 (1983).
Boger et al., "Mode of Action of Nitrodiphenylethers Affecting Pigments and Membrane Integrity", IUPAC Pesticide Chemistry, vol. 3, 97–102 (1983).
Boger et al., "Structure and Activity in Herbicidal Bleaching", IUPAC Pesticide Chemistry, 321–326 (1983).
Boger et al., "Formation and Degradation of Photosynthesis Membranes Determined–Labeled Sulfotyped", Plant Science Letters, 24, 347–352 (1982).
Dictionary of Microbiology, p. 233, 1980.
Kull et al., Applied Microbiology 9, 538 (1961).

Primary Examiner—William R. Dixon, Jr.
Assistant Examiner—Anthony J. Green
Attorney, Agent, or Firm—Michael B. Fein

[57] ABSTRACT

A synergistic antialgal composition comprising substituted fluoroalkyl diphenylethers and lysozyme in a ratio to each other which exhibits synergism is disclosed. A particularly effective combination is based on oxyfluorfen and lysozyme for use in protecting aqueous systems, such as latices and cooling water systems, from algal growth.

21 Claims, No Drawings

ANTIALGAL COMPOSITIONS COMPRISING DIPHENYLETHERS AND LYSOZYME, METHODS OF CONTROLLING ALGAE, AND COATING COMPOSITIONS COMPRISING THE ANTIALGAL COMPOSITIONS

BACKGROUND OF THE INVENTION

1. Field of the Invention

The present invention relates to antialgal compositions, methods of controlling algae, and coating compositions comprising the antialgal compositions.

2. Description of the Prior Art

The presence of algae in various aqueous systems such as latices, paints, coatings, cooling water systems, decorative ponds and the like, can cause deterioration or disfigurement of these systems. For example, painted surfaces may be disfigured by the unsightly buildup of algae, thus detracting from the overall aesthetics of the painted article; cooling towers may lose efficiency due to the buildup of algae on surfaces, thus reducing the heat transfer capabilities of the tower. It is conventional to practice methods which inhibit the algal deterioration of such systems by incorporating a variety of additives or combination of additives that are characterized by having antialgal activity.

A wide variety of materials have been used to control algae in different environments, some of which are: chlorine/bromine compounds, glutaraldehyde, isothiazolones, organotin formulations, copper salts, quaternary ammonium compounds (S. D. Strauss and P. R. Puckorius in *J. Power*, S1, June 1984), and triazines. Each has deficiencies related to toxicity, pH and temperature sensitivity, limited effectiveness, chemical stability, and/or compatibility.

Different diphenylethers ("DPEs") have been found to have widely different antimicrobial properties. See, for example, halogenated hydroxy (acyloxy) DPEs (U.S. Pat. Nos. 3,772,445; 3,908,019), and nitro/trifluoromethyl DPEs (U.S. Pat. No. 4,112,002).

U.S. Pat. No. 3,787,217 and Japanese Kokai Patent Application 48-48624 to Nitta et al are directed towards the use of halogenated and alkyl substituted DPEs as paint antifouling agents and disclose the use of these materials to control growth of clams, barnacles, and shellfish larvae at 0.5–1.0 dosage levels.

Great Britain Paten 1,592,011 to Ciba-Geigy discloses the use of DPEs containing amino (or substituted amino) or hydroxy (or ester derivatives of organic/inorganic acids) substituents as algicides, particularly dichloro- and trichloro-substituted DPEs.

Lysozyme is an enzyme found in egg whites and acts as a mild antiseptic towards certain bacteria (*Dictionary of Microbiology*, p. 233, 1980, John Wiley & Sons). Lysozyme is composed of 129 aminoacid units and has a molecular weight of 14,500. Although lysozyme is known to have certain bactericidal properties, e.g., cheese making, its use as an antialgal agent has not been disclosed.

Based on the aforementioned performance deficiencies of conventional antialgal compounds there is a need for more effective antialgal agents that can be used at lower dosage rates, thus being more cost effective for the end user, reducing the pollution load on the affected environmental systems, and reducing the side effects to nearby non-target organisms, such as fish, useful crops, etc.

SUMMARY OF THE INVENTION

It is an object of this invention to provide a method of controlling algae at very low levels of active ingredient. It is a further object to use compositions which are compatible with a variety of systems susceptible to deterioration by algae. Another object is to provide a method of controlling algae in cooling towers, paints, marine antifoulant coatings, spray washes, swimming pools, coatings, decorative ponds and the like, without objectionable by-product odors, discoloration, or otherwise detrimental effects on the treated (and controlled) systems. These objects, and others which will become apparent from the following disclosure, are achieved by the present invention which is, in one aspect a composition useful for controlling algae comprising (A) a compound of the formula $$F_pH_mC_n-\underset{X^2}{\overset{X^1}{\bigcirc}}-O-\underset{Z}{\bigcirc}-NO_2$$

wherein
- $X^1$, $X^2$ are independently selected from hydrogen, halogen, trihalomethyl, cyano, or $(C_1-C_4)$alkyl, and
- $Z$ is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or substituted lower alkyl amino, $R^2O$ in which $R^2$ represents a hydrogen atom or an ester bonded acid radical of an inorganic or organic oxyacid;
- p is an integer from 1 to $2n+1$;
- m is an integer of 0 to $2n$;
- n is an integer of 1 to 5;

$$m+p=2n+1$$

and (B) lysozyme.

In another aspect, the invention comprises a method of controlling algae comprising using an effective amount of the aforementioned composition.

Another aspect of the invention is a method of controlling algae in cooling tower water comprising maintaining a concentration of the aforementioned composition in the water.

In another aspect, the invention comprises a method of imparting algal resistance to a coating or impregnant composition comprising incorporation of the antialgal composition in the coating or impregnant.

The invention also comprises algae-resistant coating or impregnant compositions and marine antifoulant compositions comprising the antialgal composition.

DETAILED DESCRIPTION OF THE INVENTION AND THE PREFERRED EMBODIMENTS

We have discovered an especially effective composition useful for controlling algae comprising (A) a compound of the formula

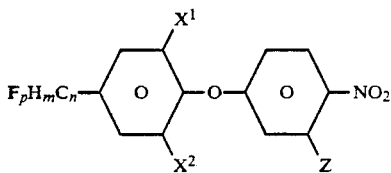

wherein
- $X^1$, $X^2$ are independently selected from hydrogen, halogen, trihalomethyl, cyano, or ($C_1$-$C_4$)alkyl, and
- Z is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or substituted lower alkyl amino, $R^2O$ in which $R^2$ represents a hydrogen atom or an ester bonded acid radical of an inorganic or organic oxyacid;
- p is an integer from 1 to $2n+1$;
- m is an integer of 0 to $2n$;
- n is an integer of 1 to 5;

$$m+p=2n+1$$

and (B) lysozyme.

Where the expression "lower" is employed in conjunction with terms, such as alkyl, alkoxy, etc., it is intended to indicate that the alkyl or alkyl portion thereof has 1 to 4 carbon atoms, i.e., ($C_1$-$C_4$).

More preferred are compositions wherein said compound (A) is of the formula

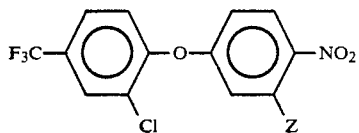

wherein Z is selected from the group consisting of lower alkoxy, carboxy or salt thereof, lower carbalkoxyalkoxy, and $-CO_2CH_2CO_2C_2H_5$.

The most preferred embodiment of compound (A) is oxyfluorfen which has the formula

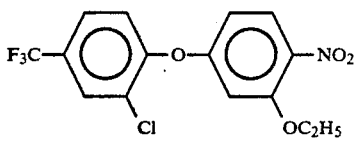

In accordance with the invention a method of controlling algae comprises using an effective amount of the aforementioned composition.

An especially useful aspect of the invention is in controlling algae in cooling tower water, and in a preferred embodiment, it is maintaining a concentration of about 0.005 to about 20 ppm of the anti-algal composition in the cooling tower water, preferably a concentration of about 0.1 to 10 ppm, and more preferably a concentration of about 0.2 to 2 ppm.

Another important utility is in imparting algal resistance to a coating or impregnant composition comprising incorporation of the composition of the invention in the coating or impregnant, preferably at a concentration of about 0.1 ppm to about 2 percent, more preferably at concentration of about 1 ppm to 1 percent, and most preferably at a concentration of about 10 to 4000 ppm. Algae-resistant coating or impregnant compositions provided by the invention preferably comprise about 0.1 ppm to about 2 percent of the antialgal composition, more preferably about 10 to 4000 ppm.

In a marine antifoulant composition, on the other hand, the antialgal composition of the invention comprises about 1 to 10 percent of the antifoulant composition.

In the protection of fabric, leather, paper or wood materials, the microbicidal composition is added at a concentration of from about 0.1 ppm to about 2 percent by weight. In aqueous media, the microbial composition comprises from about 0.005 ppm to about 1 percent of the aqueous system depending on the specific end use; for example, in cooling water tower applications and with pulp or paper manufacturing processes, the microbicidal composition is added at a concentration from about 0.1 to about 1000 ppm by weight and in the protection of solid surfaces by the application of algicidal washes.

The algal resistant compositions can also be used in construction products such as stucco, roof mastics, wall mastics, and masonry coatings for algae protection; in clear finishes and coatings to protect underlying substrates from algae; for algae control in aquaculture, including aquaria, fish hatcheries, shrimp ponds, finfish ponds, mollusc and crustacean cultivation; for algae control in recreational and decorative bodies of water such as swimming pools, lakes, fountains and decorative ponds; for algae control in bodies of water for industrial or municipal use, such as settling or separation ponds, waste treatment ponds, and water reservoirs; for algae control in hydroponic farming; for algae control in processing and manufacture of pulp and paper products; for inclusion in plastics or in coatings for plastics to protect against algae; and in plastics or coatings for plastics for swimming pool liners.

We prefer antialgal compositions wherein the weight ratio of (A) to (B) is from about 0.005/1 to about 10/1. Most preferably, we prefer ratios from about 0.001/1 to about 1/1.

Recent advances in molecular biology and taxonomy have provided for the distinction of photosynthetic procaryotic bacteria versus eucaryotic aglae. In the past literature, the term "blue-green algae" made reference to a group of microorganisms which possessed chlorphyll and appeared blue-green in color. More recent textbooks on microbiology (*Biology of Microorganisms*, T. D. Brock, D. W. Smith, and M. T. Madigan, Prentice Hall, Inc., 1984) have distinguished these organisms from eucaryotic algae, such as the green algae, and considered them to be most appropriately classified as "blue-green bacteria" or "cyanobacteria". This distinction is made since the cell architecture more closely resembles the procaryotic bacteria than euaryotic algae. Therefore, we refer herein to photosynthetic blue-green microorganisms as cyanobacteria or blue-green bacteria.

The following examples represent just a few of the many uses and compounds of the invention. They are intended to be illustrative but not limiting. Various modifications, alternatives, and improvements should become apparent to those skilled in the art without departing from the spirit and scope of the invention.

EXAMPLES

A. General Procedure

MIC values represents the Minimum Inhibitory Concentration. This is defined as the lowest level of compound required to completely inhibit (repress) the growth of a given organism.

A synergistic effect is defined as the response of two variables which is greater than the sum of both parts alone. Synergy was determined from combination studies with two compounds by the method of calculation described by F. C. Kull, P. C. Eisman, H. D. Sylwestrowics and R. K. Mayer, *Applied Microbiology* 9,538 (1961):

$$\frac{Q_a}{Q_A} + \frac{Q_b}{Q_B} = \text{synergism index } (SI)$$

where:
- $Q_A$ = quantity of compound A, acting alone, producing an end point (MIC)
- $Q_a$ = quantity of compound A, in mixture, producing an end point (MIC)
- $Q_B$ = quantity of compound B, acting alone, producing an end point (MIC)
- $Q_b$ = quantity of compound B, in mixture, producing an end point (MIC)

The following SI values may be attained:
- SI > 1 represents antagonistic effect,
- SI = 1 represents additive effect,
- SI < 1 represents synergy.

Efficacy studies were conducted on a variety of microorganisms with oxyfluorfen and lysozyme mixtures. The MIC studies were conducted using microtiter plate assays. In this method, a wide range of concentrations was tested by preparing two-fold serial dilutions of the compound in 96-well plastic microtiter plates. All liquid media transfers were performed with calibrated single or multichannel digital pipetters. Stock solutions of compounds were prepared in appropriate solvents and dispensed to the growth medium. All subsequent dilutions in plates were made using the desired growth medium; total volume of liquid in each well was 100 μl. Each plate contained a concentration of both compounds made by serially titrating equal volumes of liquids in two directions in the microtiter plate. Each plate contained a control row for each combination (one component only), hence, the individual compound MIC values were also determined.

The pure cultures used in this study were obtained from the Culture Collection of Algae at the University of Texas at Austin (UTEX). Mixed cooling tower cultures were obtained from surface scrapings of industrial cooling towers. Microorganisms used as inocula were cultured in shaken liquid culture (Bristol's medium, pH 7.0, 25 C, *Journal of Phycology*, 23 s, 1–47, 1987 or Modified Allen's Media Formulation, described below) for one week or as needed to attain a desired cell mass. The cultures were then incoulated into the microtiter plates using a 96-prong multiple inoculator (5 μl inoculum); each well received a standard suspension of biomass (5% inoculum). Plates were incubated at 25° C. under constant illumination (500 ft candles). The extend of growth was determined under low magnification with the aid of microtiter plate reader. Growth in each cell was monitored periodically and growth/no-growth was recorded after 14 or 21 days. Results of each study were evaluated by calculating synergy index values (SI, previously described).

B. Preparation of Modified Allen's Media Formulation (pH 6.3)

| Component | Concentration (mg/l) |
|---|---|
| $NaNO_3$ | 250 |
| $CaCl_2(2H_2O)$ | 31 |
| $MgSO_4(7H_2O)$ | 75 |
| NaCl | 25 |
| $KH_2PO_4$ | 175 |
| $K_2HPO_4$ | 75 |
| $FeCl_3(6H_2O)$ | 7.5 |
| $Na_2(EDTA)$ | 10.3 |
| $Na_2B_4O_7(10H_2O)$ | 2.25 |
| $MnCl_2(4H_2O)$ | 0.90 |
| $ZnCl_2(7H_2O)$ | 0.11 |
| $CuCl_2(2H_2O)$ | 0.025 |
| $Na_2MoO_4(2H_2O)$ | 0.015 |
| $VOSO_4(2H_2O)$ | 0.015 |
| $CoCl_2(6H_2O)$ | 0.005 |

EXAMPLE 1

Using a pure culture of Osilliatora sp (blue green), various combinations of Compound A, oxyfluorfen (acetone solution) and Compound B, lysozyme (Grade 1 from Sigma Chemical Co., 58, 100 units/mg) were subjected to MIC determinations (Bristol's Medium).

| $Q_a$ | $Q_b$ | $Q_a/Q_b$ | SI |
|---|---|---|---|
| 0 | 1250 ($Q_B$) | — | 1.0 |
| 0.5 | 625 | 1/1250 | 0.53 |
| 1 | 625 | 1/625 | 0.56 |
| 2 | 625 | 1/312 | 0.62 |
| 4 | 625 | 1/156 | 0.75 |
| 0.5 | 312 | 1/625 | 0.28 |
| 1 | 312 | 1/312 | 0.31 |
| 2 | 312 | 1/156 | 0.37 |
| 4 | 312 | 1/99 | 0.50 |
| 8 | 312 | 2/98 | 0.75 |
| 0.5 | 156 | 1/312 | 0.16 |
| 1 | 156 | 1/156 | 0.19 |
| 2 | 156 | 1/99 | 0.25 |
| 4 | 156 | 2/98 | 0.37 |
| 8 | 156 | 5/95 | 0.62 |
| 0.5 | 78 | 1/156 | 0.09 |
| 1 | 78 | 1/99 | 0.12 |
| 2 | 78 | 2/98 | 0.19 |
| 4 | 78 | 5/95 | 0.31 |
| 8 | 78 | 9/91 | 0.56 |
| 2 | 39 | 5/95 | 0.16 |
| 4 | 39 | 9/91 | 0.28 |
| 8 | 39 | 17/83 | 0.53 |
| 16 ($Q_A$) | 0 | — | 1.0 |

EXAMPLE 2

In a manner similar to EXAMPLE 1, another MIC study was conducted with Compound A, oxyfluorfen (acetone solution) and Compound B, lysozyme with *Scenedesmus quadri caudra* (green algae) in modified Allen's medium.

| $Q_a$ | $Q_b$ | $Q_a/Q_b$ | SI |
|---|---|---|---|
| 0 | >2500 ($Q_B$) | — | 1.0 |
| 0.00062 | 1250 | ½ × 10⁶ | <0.62 |
| 0.00125 | 1250 | 1/1 × 10⁶ | <0.75 |
| 0.00062 | 625 | 1/1 × 10⁶ | <0.37 |
| 0.00125 | 625 | 1/5 × 10⁵ | <0.5 |

-continued

| $Q_a$ | $Q_b$ | $Q_a/Q_b$ | SI |
|---|---|---|---|
| 0.0025 | 625 | $1/2.5 \times 10^5$ | <0.75 |
| 0.00062 | 312 | $1/5 \times 10^5$ | <0.25 |
| 0.00125 | 312 | $1/2.5 \times 10^5$ | <0.37 |
| 0.0025 | 312 | $1/1.2 \times 10^5$ | <0.62 |
| 0.00062 | 156 | $1/2.5 \times 10^5$ | <0.19 |
| 0.00125 | 156 | $1/1.2 \times 10^5$ | <0.31 |
| 0.0025 | 156 | $1/6 \times 10^4$ | <0.56 |
| 0.00062 | 78 | $1/1.2 \times 10^5$ | <0.16 |
| 0.00125 | 78 | $1/6 \times 10^4$ | <0.28 |
| 0.0025 | 78 | $1/3 \times 10^4$ | <0.53 |
| 0.0062 | 39 | $1/6 \times 10^4$ | <0.15 |
| 0.00125 | 39 | $1/3 \times 10^4$ | <0.27 |
| 0.0025 | 39 | $1/1.6 \times 10^4$ | <0.52 |
| 0.005 ($Q_A$) | 0 | — | 1.0 |

EXAMPLE 3

In a manner similar to EXAMPLE 1, a mixed cooling tower algae was used with various combinations of Compound A, oxyfluorfen (acetone solution) and Compound B, lysozyme (Bristol's Medium).

| $Q_a$ | $Q_b$ | $Q_a/Q_b$ | SI |
|---|---|---|---|
| 0 | >2500 ($Q_B$) | — | 1.0 |
| 0.006 | 250 | 1/40,000 | <0.60 |
| 0.006 | 125 | 1/20,000 | <0.55 |
| 0.012 | 250 | 1/20,000 | <0.60 |
| 0.012 | 125 | 1/10,000 | <0.55 |
| 0.012 | 64 | 1/5,000 | <0.52 |
| 0.012 | 32 | 1/2,500 | <0.26 |
| 0.012 | 16 | 1/1,250 | <0.26 |
| 0.025 ($Q_A$) | 0 | — | 1.0 |

We claim:

1. A microbicidal composition useful for controlling algae comprising a synergistic mixture a first component of which is (A) a compound of the formula $$F_pH_mC_n\text{-}\underset{X^2}{\overset{X^1}{\bigcirc}}\text{-}O\text{-}\underset{Z}{\bigcirc}\text{-}NO_2$$

wherein
$X^1$, $X^2$ are independently selected from hydrogen, halogen, trihalomethyl, cyano, or ($C_1$-$C_4$)alkyl, and
Z is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or substituted lower alkyl amino, $R^2O$ in which $R^2$ represents a hydrogen atom or an ester bonded acid radical of an inorganic or organic oxyacid;
p is an integer from 1 to $2n+1$;
m is an integer of 0 to $2n$;
n is an integer of 1 to 5;

$m+p=2n+1$ and a second component of which is (B) lysozyme wherein the ratio of the first component to the second component is in a range of from about 0.0005/1 to about 10/2.

2. The composition according to claim 1 wherein the first component is of the formula $$F_3C\text{-}\underset{Cl}{\bigcirc}\text{-}O\text{-}\underset{Z}{\bigcirc}\text{-}NO_2$$

wherein Z is selected from the group consisting of lower alkoxy, lower carboxy or salt thereof, lower carbalkoxyalkoxy, and $-CO_2CH_2CO_2C_2H_5$.

3. The composition according to claim 1 wherein the first component is oxyfluorfen of the formula $$F_3C\text{-}\underset{Cl}{\bigcirc}\text{-}O\text{-}\underset{OC_2H_5}{\bigcirc}\text{-}NO_2$$

and the ratio of the first component to the second component is in the range from about 0.001/1 to about 1/1.

4. The composition of claim 1 wherein the ratio of the first component to the second component is in the range from about 0.001/1 to about 1/1.

5. A coating or impregnant composition comprising from about 0.1 ppm to about 2 percent by weight of the composition of claim 1.

6. A marine antifoulant composition comprising about 1-10 percent by weight of the composition of claim 1.

7. An algae-resistant stucco, roof mastic, wall mastic, or masonry coating comprising an effective amount to control algae of the composition of claim 1.

8. An algae-resistant plastic composition comprising an effective amount to control algae of the composition of claim 1.

9. A method for inhibiting the growth of algae in a locus subject to contamination by algae, which comprises incorporating onto or into the locus, in an amount which is effective to adversely affect the growth of algae, the composition of claim 1.

10. The method of claim 9 wherein the locus is an aqueous medium and the composition is used in an amount from about 0.1 ppm to about 1 percent by weight.

11. The method of claim 9 wherein the locus is a coating or impregnant composition and the composition of claim 1 is used in an amount from about 0.1 ppm to about 2 percent by weight.

12. The method of claim 9 wherein he locus is a marine antifoulant composition and the composition of claim 1 is used in an amount from about 1 to about 10 percent by weight.

13. The method of claim 9 wherein the locus is a pulp or paper manufacturing processing and the composition is used in an amount from about 0.1 to about 1000 ppm by weight.

14. The method of claim 9 wherein the locus is cooling tower water and the composition is used in an amount from about 0.005 to about 20 ppm by weight.

15. The method of claim 9 wherein the locus is fabric, leather, paper or wood and the composition is used in an amount from about 0.1 ppm to about 2 percent by weight.

16. The method of claim 9 wherein the locus is selected from the group consisting of settling ponds, separation ponds, waste treatment ponds, spray ponds, and water treatment ponds.

17. The method of claim 9 comprising controlling the growth of algae in hydroponic farming.

18. The method of claim 9 wherein the locus is selected from the group consisting of aquaculture, aquaria, fish hatcheries, shrimp ponds, finfish ponds, mollusc cultivation, and crustacean cultivation.

19. The method of claim 9 wherein the locus is selected from the group consisting of swimming pools, lakes, spray ponds, fountains and decorative ponds.

20. Plastic swimming pool liner comprised of plastic composition according to claim 8.

21. Plastic coated with a coating composition according to claim 5.

* * * * *